(12) United States Patent
Gagne-Keats

(10) Patent No.: US 10,440,544 B2
(45) Date of Patent: Oct. 8, 2019

(54) HIGH-FREQUENCY MOTION SENSOR MODULES FOR ELECTRONIC DEVICES

(71) Applicant: Essential Products, Inc., Palo Alto, CA (US)

(72) Inventor: Jason Sean Gagne-Keats, Cupertino, CA (US)

(73) Assignee: ESSENTIAL PRODUCTS, INC., Palo Alto, CA (US)

( * ) Notice: Subject to any disclaimer, the term of this patent is extended or adjusted under 35 U.S.C. 154(b) by 0 days.

(21) Appl. No.: 16/021,457

(22) Filed: Jun. 28, 2018

(65) Prior Publication Data

US 2019/0007816 A1    Jan. 3, 2019

Related U.S. Application Data

(60) Provisional application No. 62/573,652, filed on Oct. 17, 2017, provisional application No. 62/528,357, filed on Jul. 3, 2017.

(51) Int. Cl.
| | |
|---|---|
| H04B 7/00 | (2006.01) |
| H04W 4/80 | (2018.01) |
| G01C 23/00 | (2006.01) |
| A61B 5/11 | (2006.01) |
| A61B 5/00 | (2006.01) |
| G01C 22/00 | (2006.01) |

(52) U.S. Cl.
CPC ............ H04W 4/80 (2018.02); A61B 5/0004 (2013.01); A61B 5/112 (2013.01); A61B 5/1118 (2013.01); A61B 5/6898 (2013.01); G01C 22/006 (2013.01); G01C 23/00 (2013.01); A61B 2560/0214 (2013.01); A61B 2562/0219 (2013.01)

(58) Field of Classification Search
CPC ...... H04W 4/80; A61B 5/0004; A61B 5/1118; A61B 2560/0214
USPC .................. 455/41.1, 41.2, 572, 127.1, 343.1
See application file for complete search history.

(56) References Cited

U.S. PATENT DOCUMENTS

| | | | |
|---|---|---|---|
| 6,771,935 B1 | 8/2004 | Leggett | |
| 7,812,597 B2 * | 10/2010 | Hubrich | G01D 5/2033 324/207.15 |
| 9,300,342 B2 | 3/2016 | Schlub et al. | |
| 10,112,075 B2 * | 10/2018 | Wisbey | A63B 24/0075 |
| 2009/0096413 A1 | 4/2009 | Partovi et al. | |
| 2010/0081473 A1 | 4/2010 | Chatterjee et al. | |
| 2010/0083012 A1 | 4/2010 | Corbridge et al. | |
| 2010/0131691 A1 | 5/2010 | Hornyak et al. | |
| 2010/0146308 A1 | 6/2010 | Gioscia et al. | |
| 2012/0095852 A1 | 4/2012 | Bauer et al. | |

(Continued)

*Primary Examiner* — Sonny Trinh
(74) *Attorney, Agent, or Firm* — Perkins Coie LLP; Michael Glenn

(57) ABSTRACT

Various embodiments concern motion sensor modules able to monitor movement. A motion sensor module can be detachably connected to an electronic device to which the motion sensor module transfers motion data. In some embodiments, the motion sensor module is connected to an electronic device associated with an individual. In other embodiments, the motion sensor module is embedded within an article of clothing worn by the individual (e.g., a shirt, swimsuit, or shoe). The motion sensor module includes at least one inertial measurement unit (IMU) that generates motion data indicative of the motion of the motion sensor module as a whole.

17 Claims, 10 Drawing Sheets

(56) References Cited

U.S. PATENT DOCUMENTS

| | | |
|---|---|---|
| 2012/0202427 A1 | 8/2012 | Gioscia et al. |
| 2013/0236192 A1 | 9/2013 | Deicke et al. |
| 2014/0009430 A1* | 1/2014 | Italia .............. G06F 3/044 |
| | | 345/174 |
| 2014/0059263 A1 | 2/2014 | Rosenberg et al. |
| 2014/0086586 A1 | 3/2014 | Voutilainen et al. |
| 2014/0267740 A1* | 9/2014 | Almomani ......... G07C 9/00182 |
| | | 348/156 |
| 2014/0295758 A1 | 10/2014 | Pedersen |
| 2014/0315592 A1 | 10/2014 | Schlub et al. |
| 2015/0057111 A1* | 2/2015 | Tremblay-Munger ................ |
| | | A63B 69/0026 |
| | | 473/446 |
| 2015/0091508 A1 | 4/2015 | Meunier et al. |
| 2015/0135239 A1* | 5/2015 | Oh .................. H04N 21/43637 |
| | | 725/81 |
| 2015/0195926 A1 | 7/2015 | Kandur Raja et al. |
| 2016/0141884 A1* | 5/2016 | Lee ..................... H02J 17/00 |
| | | 307/104 |
| 2016/0190861 A1 | 6/2016 | Cha |
| 2016/0375779 A1* | 12/2016 | Wang ..................... B64F 1/36 |
| | | 701/2 |
| 2017/0120105 A1* | 5/2017 | Taniguchi .......... G06K 9/00342 |
| 2017/0126268 A1 | 5/2017 | Evans V et al. |
| 2017/0149474 A1 | 5/2017 | Kim |
| 2017/0216672 A1* | 8/2017 | Wisbey .............. G09B 19/003 |
| 2017/0223160 A1* | 8/2017 | Duddy ................ H04M 1/0277 |
| 2017/0272113 A1 | 9/2017 | Evans et al. |
| 2018/0041617 A1* | 2/2018 | Shamsoddini ........... H01Q 9/42 |

\* cited by examiner

HIGH-FREQUENCY MOTION SENSOR MODULES FOR ELECTRONIC DEVICES

CROSS-REFERENCE TO RELATED APPLICATIONS

This application claims priority to and the benefit of U.S. Provisional Patent Application No. 62/573,652, titled "HIGH-FREQUENCY MOTION SENSOR MODULES FOR ELECTRONIC DEVICES" and filed Oct. 17, 2017, and U.S. Provisional Patent Application No. 62/528,357, titled "TECHNOLOGIES FOR HANDHELD DEVICES" and filed Jul. 3, 2017, each of which is incorporated herein by reference in its entirety.

RELATED FIELD

Various embodiments generally concern motion sensor modules for monitoring movement.

BACKGROUND

Motion trackers (also referred to as "activity trackers" or "fitness trackers") are devices for monitoring motion-related metrics. Examples of motion-related metrics include total distance moved, the number of steps taken, etc. Over time, a motion tracker will generate motion data indicative of movement.

However, the motion tracker typically does not examine the motion data in depth. Instead, the motion tracker transfers the motion data to another electronic device (e.g., a mobile phone, tablet computer, or network-accessible server).

Some motion trackers can be connected to electronic devices through a wired connection. For example, a motion tracker may be physically coupled to an electronic device via a 3.5 millimeter headphone jack, Universal Serial Bus (USB) port, proprietary connector such as an Apple Lightning® connector, etc. Other motion trackers are connected to electronic devices through a wireless connection. For example, a motion tracker may be wirelessly coupled to an electronic device via a Bluetooth® chip, Wi-Fi chip, Near Field Communication (NFC) chip, etc.

A wired connection ensures that a motion tracker can transfer data at a relatively high speed. However, wired connections may be undesirable from an aesthetic perspective. Moreover, wired connections are often impractical in certain situations (e.g., when a clear channel between the motion tracker and the electronic device is not present).

Wireless connections, meanwhile, may experience poor connectivity and/or limited bandwidth in some situations. Both of these issues can impact an individual's ability to utilize a motion tracker. Motion trackers also typically require a power source that requires its own wired connection (e.g., a dedicated AC/DC adapter) or a power source that must be periodically replaced (e.g., a battery).

SUMMARY

Mechanisms for securely attaching an accessory to a wireless accessory bus of an electronic device are described herein. The wireless accessory bus enables data to be wirelessly transmitted between the accessory and the electronic device when the accessory and the electronic device are located within close proximity to one another. For example, data may be automatically transferred when the accessory is detachably connected to the wireless accessory bus of the electronic device. Power could also be wirelessly transferred from the electronic device to the accessory, or vice versa.

An example of an accessory is a motion sensor module able to monitor movement. The motion sensor module can be detachably connected to an electronic device to which the motion sensor module transfers motion data. In some embodiments, the motion sensor module monitors movement of the electronic device. For example, the motion sensor module may be connected to a mobile phone or a fitness tracker. In other embodiments, the motion sensor module monitors the movement of an individual. For example, the motion sensor module may be embedded within an article of clothing (e.g., a shirt or shoe).

The motion sensor module includes at least one inertial measurement unit (IMU) configured to generate motion data indicative of the motion of the motion sensor module as a whole. An IMU can include an accelerometer, gyroscope, magnetometer, or any combination thereof. Generally, the IMU has a sample rate of at least 100 kilohertz (kHz) that enables personalized feedback regarding gait, health status, etc. For example, a computer program examining the motion data may be able to identify the type of step taken by an individual, rather than simply detecting that the individual took a step.

BRIEF DESCRIPTION OF THE DRAWINGS

Various features and characteristics of the technology will become more apparent to those skilled in the art from a study of the Detailed Description in conjunction with the drawings. Embodiments of the technology are illustrated by way of example and not limitation in the drawings, in which like references may indicate similar elements.

Figure 1:
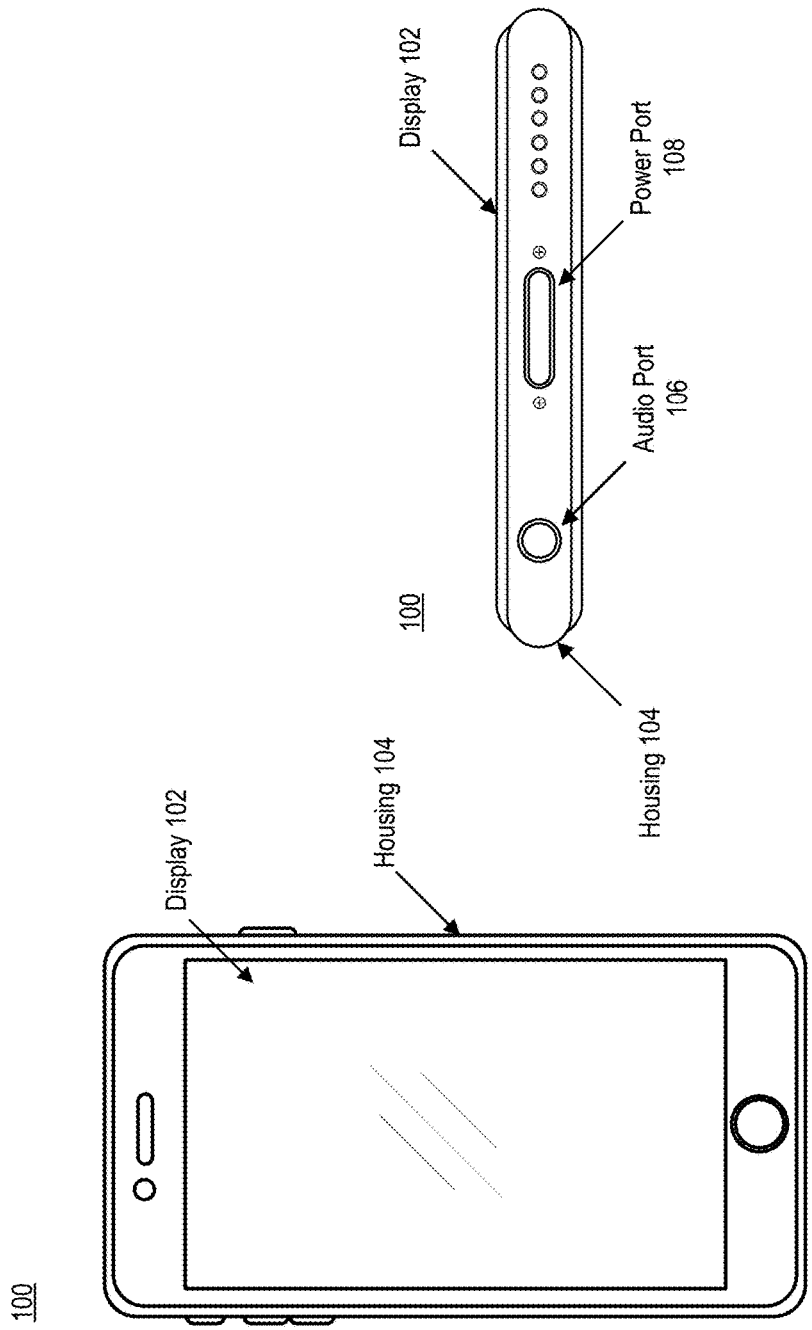
FIG. 1A is a front view of a conventional mobile phone that includes a display disposed within a housing 104 that protects various internal components (e.g., sensors, connectors, power supply).
FIG. 1B is a bottom view of the conventional mobile phone 100 that includes an audio port 106 and a power port 108.

The drawings depict various embodiments for the purpose of illustration only. Those skilled in the art will recognize that alternative embodiments may be employed without departing from the principles of the technology. Accordingly, while specific embodiments are shown in the drawings, the technology is amenable to various modifications.

DETAILED DESCRIPTION

Mechanisms for securely attaching an accessory to a wireless accessory bus of an electronic device are described herein. The wireless accessory bus enables data to be wirelessly transmitted between the accessory and the electronic device when the accessory and the electronic device are located within close proximity to one another. For example, data may be automatically transferred when the accessory is detachably connected to the wireless accessory bus of the electronic device. Power could also be wirelessly transferred from the electronic device to the accessory, or vice versa.

An example of an accessory is a motion sensor module able to monitor movement. The motion sensor module can be detachably connected to an electronic device to which the motion sensor module transfers motion data. In some embodiments, the motion sensor module monitors movement of the electronic device. For example, the motion sensor module may be connected to a mobile phone or a fitness tracker. In other embodiments, the motion sensor module monitors the movement of an individual. For example, the motion sensor module may be embedded within an article of clothing (e.g., a shirt or shoe).

The motion sensor module includes at least one inertial measurement unit (IMU) configured to generate motion data indicative of the motion of the motion sensor module as a whole. An IMU can include an accelerometer, gyroscope, magnetometer, or any combination thereof. Generally, the IMU has a sample rate of at least 100 kilohertz (kHz) that enables personalized feedback regarding gait, health status, etc. For example, a computer program examining the motion data may be able to identify the type of step taken by an individual, rather than simply detecting that the individual took a step.

These mechanisms can be used with any electronic device (also referred to as a "user device") for which it is desirable to transfer data at high speeds, such as a personal computer, tablet computer, personal digital assistant (PDAs), mobile phone, game console (e.g., Sony PlayStation® or Microsoft Xbox®), mobile gaming device (e.g., Sony PlayStation Portable™ or Nintendo 3DS™), music player (e.g., Apple iPod Touch®), wearable electronic device (e.g., a watch or fitness band), network-connected ("smart") device (e.g., a television or home assistant device), virtual/augmented reality system (e.g., a head-mounted display such as Oculus Rift® and Microsoft Hololens®), or some other electronic device.

Terminology

References in this description to "an embodiment" or "one embodiment" means that the particular feature, function, structure, or characteristic being described is included in at least one embodiment. Occurrences of such phrases do not necessarily refer to the same embodiment, nor are they necessarily referring to alternative embodiments that are mutually exclusive of one another.

Unless the context clearly requires otherwise, the words "comprise" and "comprising" are to be construed in an inclusive sense rather than an exclusive or exhaustive sense (i.e., in the sense of "including but not limited to"). The terms "connected," "coupled," or any variant thereof is intended to include any connection or coupling, either direct or indirect, between two or more elements. The coupling/connection can be physical, logical, or a combination thereof. For example, two devices may be electrically or communicatively coupled to one another despite not sharing a physical connection.

When used in reference to a list of multiple items, the word "or" is intended to cover all of the following interpretations: any of the items in the list, all of the items in the list, and any combination of items in the list.

Wireless Accessory Bus Overview

FIG. 1A is a front view of a conventional mobile phone 100 that includes a display 102 disposed within a housing 104 that protects various internal components (e.g., sensors, connectors, power supply). The housing 104 is typically comprised of a protective substrate, such as metal, glass, or plastic. In some embodiments, the display 102 is touch sensitive. Thus, the display 102 may be configured to generate signals in response to an individual contacting the outer surface of the display 102.

The mobile phone 100 could also include other features as well, such as a camera and a touch-sensitive button that are offset from the display 102. The camera and/or touch-sensitive button may be located within an opaque border that surrounds the display 102 and does not respond to user interactions (i.e., is not touch sensitive). The opaque border is often used to hide various components that reside within the mobile phone 100.

FIG. 1B is a bottom view of the conventional mobile phone 100 that includes an audio port 106 and a power port 108. The audio port 106 is a receptacle or jack that can be used to transmit analog signals (e.g., audio). More specifically, the audio port 106 typically two, three, or four contacts that enable audio signals to be readily transmitted when an appropriate plug is inserted into the audio port 106. For example, most speakers and headphones include a plug designed for a 3.5 millimeter (mm) audio jack.

The power port 108 enables the conventional mobile phone 100 to be physically connected directly to a power source. For example, the power port 108 may be capable of interfacing with a Universal Serial Bus (USB) adapter (e.g., a micro-USB adapter), a 30-pin adapter, or a proprietary adapter (e.g., an Apple Lightning® cable). Together, the audio port 106 and the power port 108 can enable accessories to be fastened directly to the conventional mobile phone 100. However, as noted above, physical connections (i.e., wired connections) are often undesirable for both aesthetic and functional reasons.

Although certain embodiments of the technology is described in conjunction with mobile phones, the technology can also be used with other electronic devices for which it is desirable to eliminate physical ports.

Figure 2:
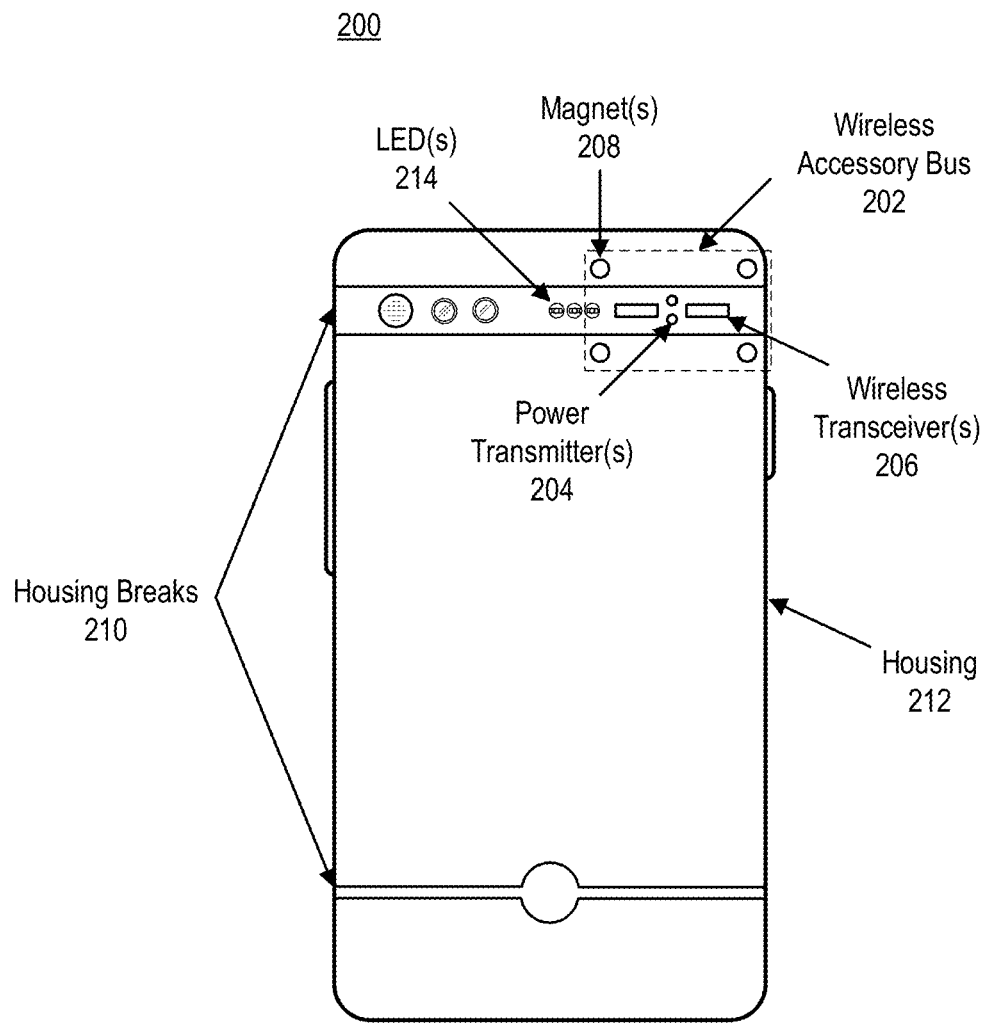
FIG. 2 is a rear view of an electronic device that includes a wireless accessory bus capable of receiving an accessory.

FIG. 2 is a rear view of an electronic device 200 that includes a wireless accessory bus 202 capable of receiving an accessory. The wireless accessory bus 202 enables data and/or power to be wirelessly transferred from the electronic device 200 to the accessory (or vice versa) when the electronic device 200 and the accessory are within close proximity to one another. For example, a bi-directional communication channel may be established when the accessory is securely attached to the wireless accessory bus 202.

As shown in FIG. 2, the term "wireless accessory bus" generally refers to an area of the electronic device 200 that is configured to securely receive an accessory. The wireless accessory bus 202 can include one or more power transmitters 204, one or more wireless transceivers 206, and/or one or more magnets 208 (collectively referred to as the "bus components").

Some of the bus components could be at least partially exposed through the housing 212. For example, the magnet(s) 208 may be exposed through opening(s) in the housing 212. Additionally or alternatively, some of the bus components could be housed entirely within the housing 212. In such embodiments, the bus components may be selected in order to compensate for signal degradation that occurs as the data signals and/or power signals travel through the housing 212 or a substrate laid within a break 210 in the housing 212. The substrate may be an optically-clear substrate, such as glass or plastic.

The power transmitter(s) 204 can be configured to transfer power from a power supply (e.g., a battery) disposed within the housing 212 to an accessory via a wired or wireless electrical coupling. For example, the power transmitter(s) 204 may include one or more electrical contacts (e.g., pin terminals) that are able to physically connect one or more corresponding electrical contacts of the accessory. As another example, the power transmitter(s) 204 may include integrated circuits (also referred to as "chips") that are able to wirelessly transmit power from the electronic device 200 to the accessory. The power transmitter(s) 204 may be configured to transmit power in accordance with the Qi standard developed by the Wireless Power Consortium or some other wireless power standard.

The wireless transceiver(s) 206 can be communicatively coupled to one or more corresponding wireless transceivers included in the accessory. For the purpose of simplification, the term "wireless transceiver" is intended to cover components that are able to transmit data, receive data, or both. Thus, a single wireless transceiver could include distinct components responsible for transmitting and receiving data.

Upon determining that an accessory has been securely attached to the wireless accessory bus 202, the wireless transceiver(s) 206 may be configured to automatically initiate a connection with the wireless transceiver(s) of the accessory. For example, if the accessory includes an IMU, then motion data may be received by the wireless transceiver(s) 206 from the accessory.

In some embodiments, a computer program associated with the accessory could be downloaded from a network-accessible environment (e.g., a digital distribution platform, such as a website or application store). Similarly, the computer program may be automatically launched in response to determining that the accessory has been securely attached to the wireless accessory bus 202. The computer program may be, for example, a web browser, desktop software program, mobile application, or over-the-top (OTT) application.

Oftentimes, the wireless accessory bus 202 includes a fastening component that enables the accessory to be detachably connected to the electronic device 200. Here, for example, magnet(s) 208 are arranged around the wireless accessory bus 202 so that the accessory is held in a predetermined orientation when secured to the electronic device 200. However, other materials/components could also be used. For example, a magnetic film may be deposited on the outer or inner surface of the housing 212. As another example, a mechanical track, clip, etc., could be affixed to the housing 212. The predetermined orientation may cause the wireless transceiver(s) 206 of the electronic device 200 to be aligned with, or disposed in close proximity to, wireless transceiver(s) of the accessory.

The housing 212 may include one or more breaks 210. These break(s) 210 may be necessary for permitting antenna(s) within the housing 212 to send/receive signals or could be included for stylistic/aesthetic purposes. The break(s) typically include a substrate layer comprised of a non-metal material, such as glass, plastic, or ceramic, that allows signals to more readily pass through.

As shown in FIG. 2, the wireless accessory bus 202 could be positioned in or near one of the break(s) 210. In such embodiments, one or more light-emitting diodes (LEDs) 214 disposed beneath the substrate layer may be configured to convey information about the electronic device 200 and/or the accessory. For example, the LED(s) 214 could illuminate when the accessory is brought near the electronic device 200, thereby indicating where the accessory should be attached. As another example, the LED(s) 214 could convey operational information such as whether the accessory is receiving sufficient power, able to transfer data signals to the electronic device 200, currently available for use, etc.

Further characteristics of the wireless accessory bus 202 are described in U.S. application Ser. No. 15/336,657, which is incorporated herein by reference in its entirety.

Motion Sensor Module Overview

Figure 3:
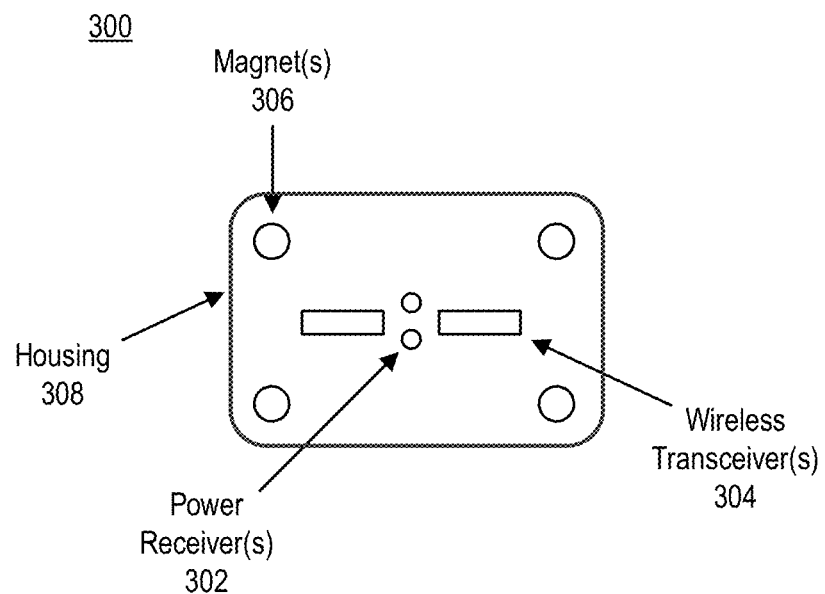
FIG. 3 depicts a motion sensor module that can be secured to an electronic device having a wireless accessory bus.

FIG. 3 depicts a motion sensor module 300 that can be secured to an electronic device having a wireless accessory bus (e.g., electronic device 200 of FIG. 2). The motion sensor module 300 can include one or more power receivers 302, one or more wireless transceivers 304, and/or one or more magnets 306 (collectively referred to as the "module components").

Some of the module components could be at least partially exposed through the housing 308. For example, the magnet(s) 306 or the power receiver(s) 302 may be exposed through opening(s) in the housing 308. In such embodiments, the housing 308 may be hermetically sealed (e.g., using an epoxy resin or rubber seals) to provide waterproof functionality. Some embodiments of the motion sensor module 300 are rated for depths of greater than 10 feet, 50 feet, 100 feet, etc.

The motion sensor module 300 and the electronic device may be capable of being repeatedly attached/detached from one another. For example, the motion sensor module 300 may include one or more fastening components that allow the motion sensor module 300 and the electronic device to be securely and detachably connected to one another. Here, the motion sensor module 300 includes magnet(s) 306. Additionally or alternatively, the motion sensor module 300 may include a magnetic film, mechanical track, clip, etc. In some embodiments, at least a portion of the housing 308 is comprised of a ferromagnetic material that enables the motion sensor module 300 to be maintained in a predetermined orientation relative to a magnet disposed within the electronic device.

The fastening component(s) are generally arranged such that they substantially align with corresponding fastening component(s) of the electronic device. For example, the motion sensor module 300 and the electronic device may include a specific number of magnets that are arranged in a substantially similar pattern. Consequently, an individual could elect to attach the motion sensor module 300 to the electronic device to initiate a transfer of motion data, and then detach the motion sensor module 300 from the electronic device for further use.

As noted above, the power receiver(s) 302 can be configured to receive power from the electronic device via a wired or wireless electrical coupling. For example, the power receiver(s) 302 may include one or more electrical contacts (e.g., pin terminals) that are arranged to physically connect to one or more corresponding electrical contacts of the electrical device. As another example, the power receiver(s) 302 may include chips that are able to receive power that is wirelessly transmitted by the electronic device.

For the purpose of simplification, motion sensor modules are typically described as having "power receivers" and electronic devices are typically described as having "power transmitters." However, those skilled in the art will recognize that power may also be transferred from a motion sensor module to an electronic device. In such embodiments, the motion sensor module may include a power transmitter and the electronic device may include a power receiver.

The wireless transceiver(s) 304 can be communicatively coupled to one or more corresponding wireless transceivers included in the electronic device. For example, the wireless transceiver(s) 304 may automatically initiate a connection with the wireless transceiver(s) of the electronic device upon being secured to a wireless accessory bus.

Figure 4:
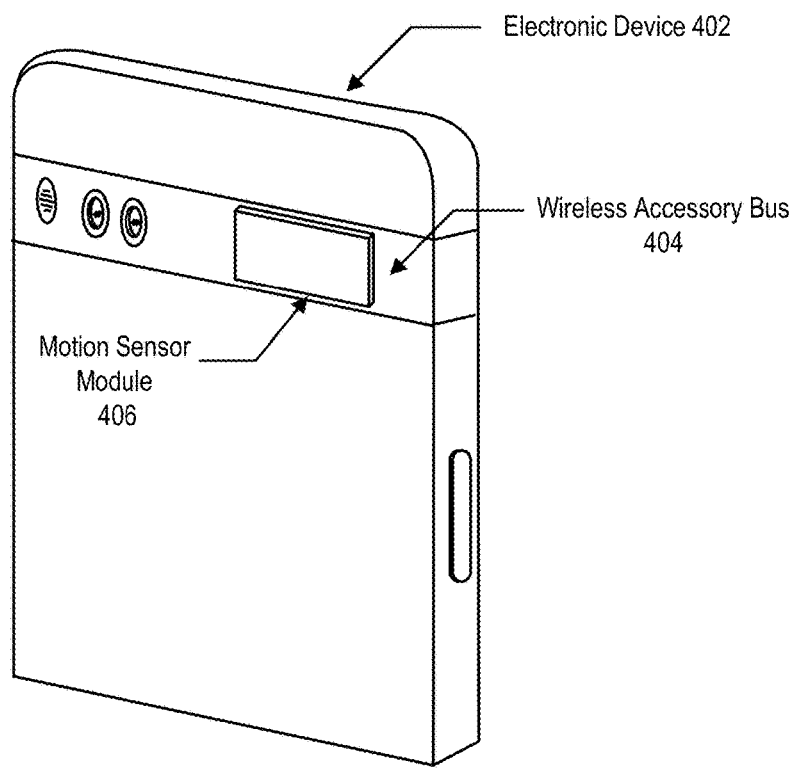
FIG. 4 illustrates how a motion sensor module can be fastened to the wireless accessory bus of an electronic device (here, a mobile phone).

FIG. 4 illustrates how a motion sensor module 406 can be fastened to the wireless accessory bus 404 of an electronic device 402 (here, a mobile phone). The motion sensor module 406 can be designed such that the motion sensor module 406 can be readily attached to (and removed from) the wireless accessory bus 404 without modification.

Moreover, the electronic device 402 can be configured to automatically establish a communication channel for transferring data between the electronic device 402 and the motion sensor module 406, as well as a power channel for transferring power between the electronic device 402 and the motion sensor module 406. Either of these channels can be automatically established after the motion sensor module 406 has been attached to the wireless accessory bus 404. Consequently, the motion sensor module 406 may begin transferring motion data immediately or soon after attachment to the wireless accessory bus 404.

Moreover, the motion sensor module 406 may continue to movement regardless of whether the motion sensor module is attached/detached from the wireless accessory bus 404 of the electronic device. Thus, in some embodiments, the motion sensor module 406 automatically ceases monitoring movement after being secured to the wireless accessory bus 404. In other embodiments, the motion sensor module 406 continues monitoring movement after being secured to the wireless accessory bus 404.

In some embodiments, a computer program associated with the motion sensor module 406 is initiated in response to determining that the motion sensor module 406 has been attached to the electronic device 402. For example, the computer program may automatically examine motion data generated by the motion sensor module 406 to estimate an activity level of the individual. Thus, the computer program may identify the number of steps taken, the type of activities performed (e.g., running, lifting, or swimming), etc. The computer program may be a web browser, desktop software program, mobile application, or OTT application.

Figure 5:
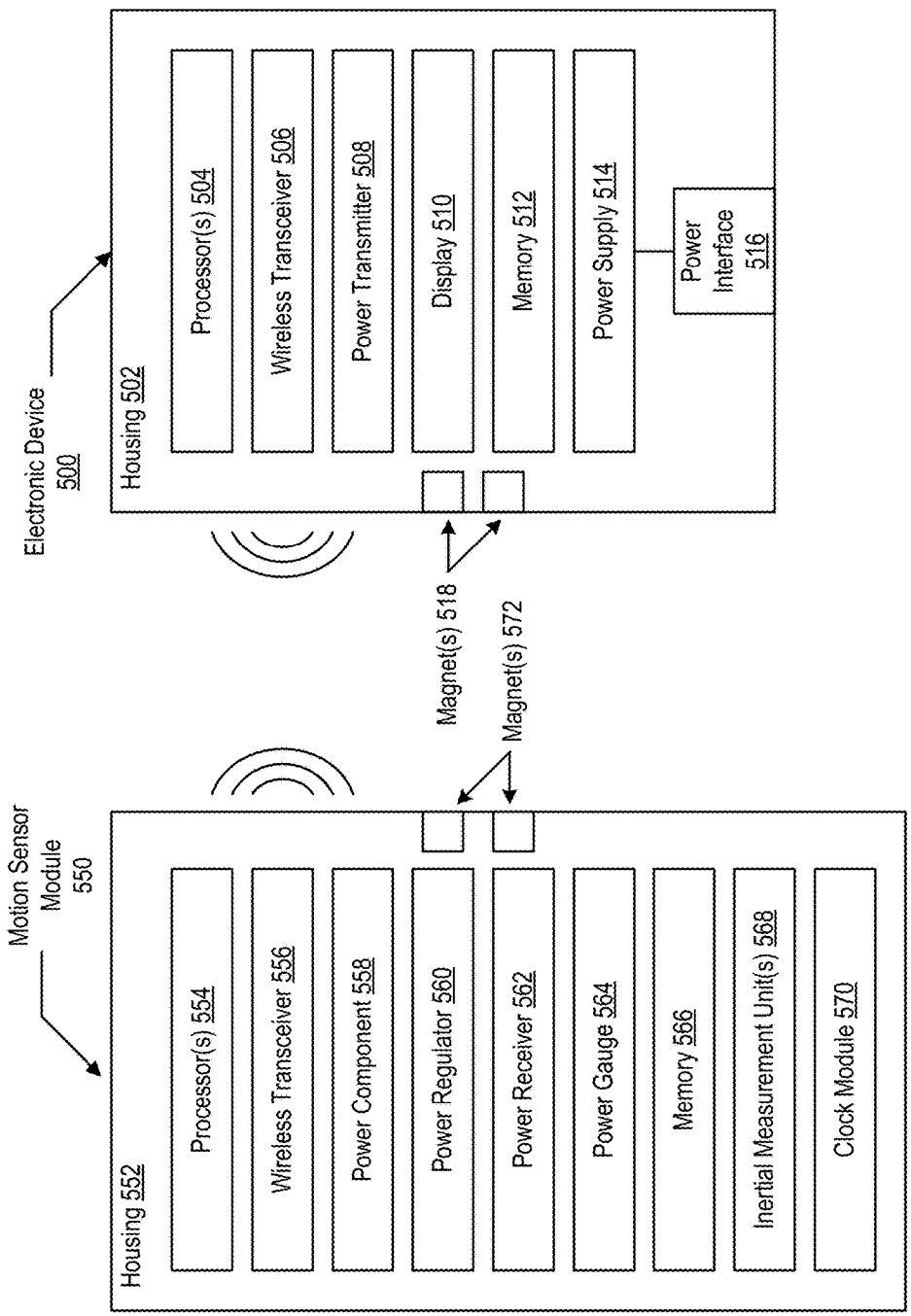
FIG. 5 is a high-level block diagram illustrating exemplary components of an electronic device and a motion sensor module.

FIG. 5 is a high-level block diagram illustrating exemplary components of an electronic device 500 and a motion sensor module 550. Embodiments of the electronic device 500 and the motion sensor module 550 can include some or all of these components, as well as other components not shown here.

The electronic device 500 can include one or more processors 504, a wireless transceiver 506, a power transmitter 508, a display 512, a memory 512, and/or a power supply 514 electrically coupled to a power interface 516. These components can be retained within a housing 502 that includes one or more magnets 518 arranged to securely receive the motion sensor module 550.

The wireless transceiver 506 can be configured to automatically establish a wireless connection with the wireless transceiver 556 of the motion sensor module 556. The wireless transceivers 506, 556 allow data to be transmitted between the electronic device 500 and the motion sensor module 550 via a wireless communication channel. For example, the wireless transceivers 506, 556 may communicate with one another using a bi-directional communication protocol, such as Near Field Communication (NFC), wireless Universal Serial Bus (USB), Bluetooth®, Wi-Fi, a cellular data protocol (e.g., 3G or 4G), a proprietary point-to-point protocol, etc.

The transfer speed may vary based on the type of wireless transceiver and the type of wireless communication channel. For example, Bluetooth® can allow transfer speeds of up to 50 megabit per second (Mbps). More specifically, Bluetooth® 3.0/4.0 typically permit transfer speeds of up to 25 Mbps, while Bluetooth® 5.0 typically permits transfer speeds of up to 50 Mbps. Although Bluetooth® may be used for negotiation establishment, these transfer speeds are achieved via a collocated Institute of Electrical and Electronics Engineers (IEEE) 802.11 communication link. Bluetooth® itself is often limited to transfer speeds of 2.1-3.0 Mbps. As another example, NFC can allow transfer speeds of up to 424 kilobit per second (kbps). As yet another example, Wi-Fi Direct® can allow transfer speeds of up to 250 Mbps.

Meanwhile, a proprietary point-to-point protocol may allow transfer speeds exceeding 1 gigabit per second (Gbps). For example, the wireless transceivers 506, 556 may include high-frequency transceivers (e.g., a 60 GHz mm-wave transceiver chipset) able to achieve transfer speeds of up to 12 Gbps. Other embodiments of the transceivers 506, 556 may be configured to achieve transfer speeds of at least 512 Mbps, 2 Gbps, 4 Gbps, etc.

In some embodiments, the wireless transceiver 506 is able to simultaneously or sequentially communicative over different wireless communication channels. For example, the wireless transceiver 506 may periodically send operational information (e.g., battery status and memory usage) to an electronic device via a Bluetooth® link. However, the wireless transceiver 506 may only send motion data to the electronic device via a high-frequency point-to-point link that permits transfer speeds exceeding 1 Gbps.

Oftentimes, the electronic device 500 will include a display 510, a memory 512, and a power supply 514 that is electrically coupled to a power interface 516 (e.g., a physical power port or a Qi-compliant wireless receiver). The memory 512 can include an operating system executable by the processor(s) 504 and one or more computer programs associated with the motion sensor module 550. The electronic device 500 may be configured to invoke a particular computer program upon determining that the motion sensor module 550 has been attached to the wireless accessory bus. For example, the electronic device 500 may invoke a mobile application able to parse motion data generated by the motion sensor module 550, determine an activity level based on the motion data, etc.

The motion sensor module 550 can include one or more processors 554, a wireless transceiver 556, a power component 558, a power regulator 560, a power receiver 562, a power gauge 564, a memory, 566, one or more inertial measurement units 568, and/or a clock module 570. These components can be retained within a housing 552 that includes one or more magnets 572 arranged so as to enable the motion sensor module 550 to be attached to the electronic device 500.

The motion sensor module 550 typically includes a power component 558 able to provide power to various internal components (e.g., the processor(s) 554 and the IMU 568). The power component 558 may be, for example, a rechargeable battery comprised of nickel-cadmium (NiCd), nickel-metal hydride (NiMH), lithium-ion (Li-ion), Li-ion polymer, etc.

The power transmitter 508 of the electronic device 500 may be configured to transfer power from the power supply 514 to the motion sensor module 550. More specifically, the power transmitter 508 may transfer power to the power receiver 562 of the of the motion sensor module 550 for storage within the power component 558. The power transmitter 508 of the electronic device 500 and the power receiver 562 of the motion sensor module 550 may be electrically coupled to one another via a physical connection (e.g., using electrical contacts) or a wireless connection (e.g., using power transmitter chips).

The motion sensor module 550 may include a power regulator 560 and/or a power gauge 564. The power regulator 560 (also referred to as a "voltage regulator") may automatically ensure that a substantially constant voltage is delivered from the power component 558 to the processor(s) 554, IMU(s) 568, etc. Thus, the power regulator 560 may stabilize the voltages used by the processor(s) 554, IMU(s) 568, etc. The power gauge 564 may determine the present state of charge of the power component 558. For example, upon determining that the power component 558 is at less than full charge, the power gauge 564 may indicate to the power receiver 562 that additional power should be received/requested from the electronic device 500.

The motion sensor module 550 also includes IMU(s) 568 configured to generate motion data indicative of motion of the motion sensor module 550. Each IMU can include an accelerometer, gyroscope, magnetometer, or any combination thereof.

Traditional fitness trackers typically have a sampling rate of approximately 100 hertz. However, the IMU(s) 568 of the motion sensor module 550 may have a sampling rate exceeding 100 kilohertz (kHz). Thus, traditional fitness trackers may generate a data sample once every hundredth of a second, while the motion sensor module 550 may generate a data sample once every hundred-thousandth of a second.

This allows the electronic device 500 (or the motion sensor module 550 itself) to not only determine when an individual took a step, but also identify certain characteristics pertaining to the step. For example, the additional data samples may permit the electronic device to discover the direction of a step, the type of step, the type of activity being performed, abnormalities in gait (which may be indicative of other health issues), sleep patterns, etc.

In some embodiments, the motion sensor module 550 also includes a clock module 570. The clock module 570 can periodically or continually generate time stamps, which can be associated with the motion data generated by the IMU(s) 568. The time stamps enable temporal alignment of the motion data. Such information permits the electronic device 500 or the motion sensor module 550 to identify time-based behavior patterns. This may enable the electronic device 500 or the motion sensor module 550 to more intelligently provide biofeedback (e.g., in the form of notifications before/after the individual wakes up, performs certain actions, etc.).

Figure 6:
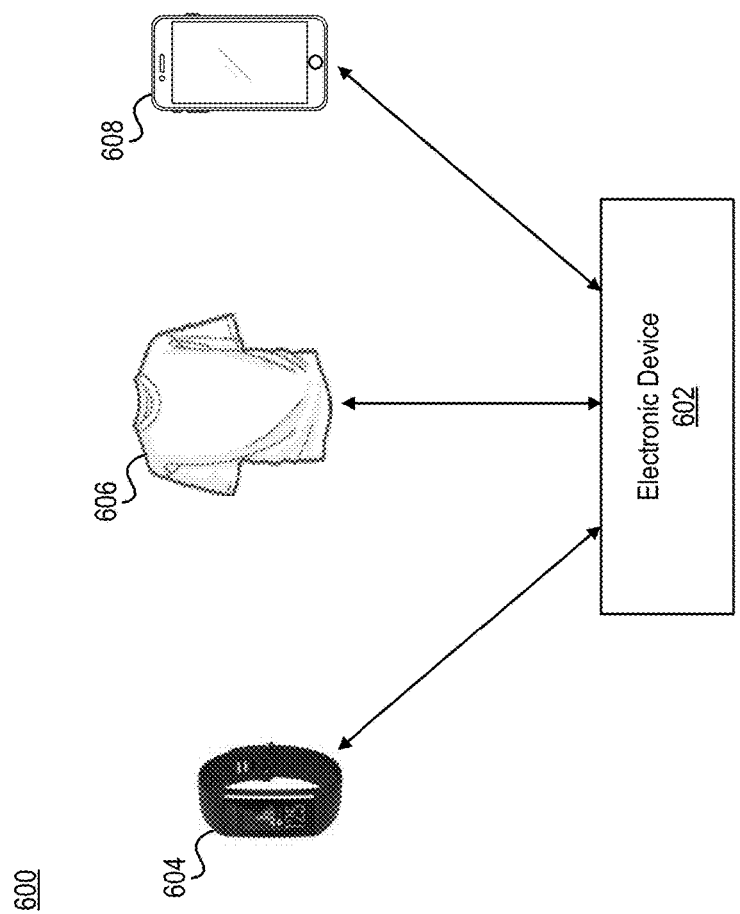
FIG. 6 depicts an example of a network environment that includes an electronic device capable of receiving motion data generated by multiple inertial measurement units (IMUs).

FIG. 6 depicts an example of a network environment 600 that includes an electronic device 602 capable of receiving motion data generated by multiple IMUs. Here, for example, at least one motion sensor module is secured to (or embedded within) a wearable electronic device 604, an article of clothing 606, and a mobile phone 608.

As noted above, each IMU can have a sampling rate exceeding 100 kHz. However, transferring these large amounts of motion data over Wi-Fi or Bluetooth® will typically take too long. Rather than require a wired connection (which may be burdensome, inconvenient, or impossible in certain situations), the motion data can instead be transferred via a wireless accessory bus. For example, an individual may be able to connect the wearable fitness device 604 or the motion sensor module(s) associated with the wearable fitness device 604 directly to the electronic device 602.

One advantage of some embodiments of the motion sensor modules introduced here is that no physical connectors are necessary (and thus no holes need to be drilled into the housing). Hence, the housing can be made entirely waterproof. Further, the housing may use plasma electrolytic oxidation (PEO) technology to create invisible antenna windows. While antennas are unable to transmit through metal, PEO technology can be used to convert a portion of a metal housing (e.g., comprised of titanium) into a radio frequency-transparent (RF-transparent) segment comprised of, for example, titanium dioxide. Thus, in some embodiments, the motion sensor module is a small titanium device that can be used to monitor movement during water-based activities (e.g., swimming and diving).

The volume of motion data collected by the electronic device 602 can enable greater resolution of user fitness, as well as enable deriving new insights into fitness and general health. For example, upon examining the volume of motion data, the electronic device 602 may be able to determine certain health-related issues (e.g., whether a toe is angled in/or, whether force is being properly distributed along the foot, whether the knee is locking during a stride).

Motion data collected by the electronic device 602 can be used to provide fitness-related advice or merely suggest that such advice should be sought out by an individual. Accordingly, in some instances the electronic device 602 may simply collect motion data from one or more motion sensor modules and direct the individual to a certain service, entity, or person (e.g., a medical professional, such as a physician, athletic trainer, or researcher). In some embodiments the electronic device 602 examines the motion data to provide personalized recommendations, while in other embodiments the electronic device 602 alerts the individual that the individual should obtain additional information, consult a medical professional, etc.

For example, motion data may indicate whether an individual is running in such a manner that the individual is likely to hurt a knee or ankle. In such embodiments, a recommendation may be provided that specifies any further action(s) necessary to address the problem(s). The range in advice given based on the motion data can vary from raw results (e.g., "Your knee impact is greater this week than last week.") to medical advice (e.g., "You should try to aim your knee outwards to avoid ligament damage.").

In some embodiments, the motion data is used to perform gait analysis. Certain gait characteristics (e.g., stride length, impact force, impact frequency) can be examined to discover whether the individual suffers from any leg-related problems. These gait characteristics may also be indicative of other health issues (e.g., cardiovascular and respiratory problems). Motion sensor modules can provide similar feedback regarding other physical activities, such as lifting, swimming, etc.

As noted above, a computer program executed by the electronic device 602 may parse, examine, and present the motion data. For example, the computer program may perform coaching feedback based on motion data generated before, during, or after athletic activities. As another example, the computer program may provide general wellness feedback based on motion data generated before, during, or after an interval of sleep.

As shown in FIG. 3, a single motion sensor module may be shaped like a rectangle. Generally, the length and width dimensions of the motion sensor module are between 1 inch and 3 inches. For example, a motion sensor module may be approximately 1 inch by 2 inches, 1.5 inches by 1.5 inches, etc. While the thickness of the motion sensor module is typically less than 0.5 inches, some embodiments of the motion sensor module have a thickness exceeding 0.5 inches.

The motion sensor module may include a fastener component (e.g., a clip, magnet, or adhesive material) that allows the motion sensor module to be readily attached to apparel or an accessory. For example, the motion sensor module could be secured to a shirt, shoe, swimming trunks, belt, wristband, etc. Thus, the motion sensor module may be worn on a shoe for lower body analysis, or the motion sensor module may be worn on a wristband similar to a watch for upper body analysis. In some embodiments, the motion sensor module includes a clip that allows the motion sensor module to be clipped to various types of clothing.

The placement of the motion sensor module along the human body can affect the type of motion data that is collected and the subsequent analysis. For example, motion sensor modules located near a foot may be able to collect gait-related motion data with less noise. As another example, motion sensor modules located near a hand may be able to more consistently detect occurrences of certain activities (e.g., swimming, golfing, and lifting)

Embodiments of the motion sensor module can be used to track a variety of movements during the performance of a variety of activities (e.g., golf, basketball, baseball, etc.). Moreover, an individual may wear multiple motion sensor modules such that, for example, motion data can be used to discern movement of a throwing arm versus movement of a foot. In such embodiments, each motion sensor module may be assigned to a particular limb so that a computer program can discern specific limbs based on the locations of the motion sensor modules and any identified movements.

After motion data has been collected from the multiple motion sensor modules, the electronic device 602 can analyze the motion data to generate a holistic picture of user movement. In some embodiments, a motion sensor module is assigned a profile related to a particular body part (e.g., a wrist, hip, or foot) or environment (e.g., running activities or swimming activities). A motion sensor module may automatically detect where it is located based on the movement data it generates because, for example, certain movements are indicative of a foot rather than an arm. Thus, a motion sensor module may automatically detect changes in location or orientation (e.g., a change in position from a waistband to a shoe). Location could also be identified after the motion data is generated.

In one example, one or more motion sensor modules are used for weightlifting analysis. The motion sensor module(s) may generate motion data that makes it possible to determine the speed of each movement when an individual picks a weight up (e.g., discern between a clean and jerk). Moreover, the motion data may make it possible to identify when the individual is likely to suffer an injury (e.g., by identifying variations in movement speed, frequency, posture, etc.). For example, upon determining that the individual is attempting to perform a squat, the motion sensor module or an electronic device can monitor motion data to identify postures in which the individual is more likely to suffer an injury.

Figure 7:
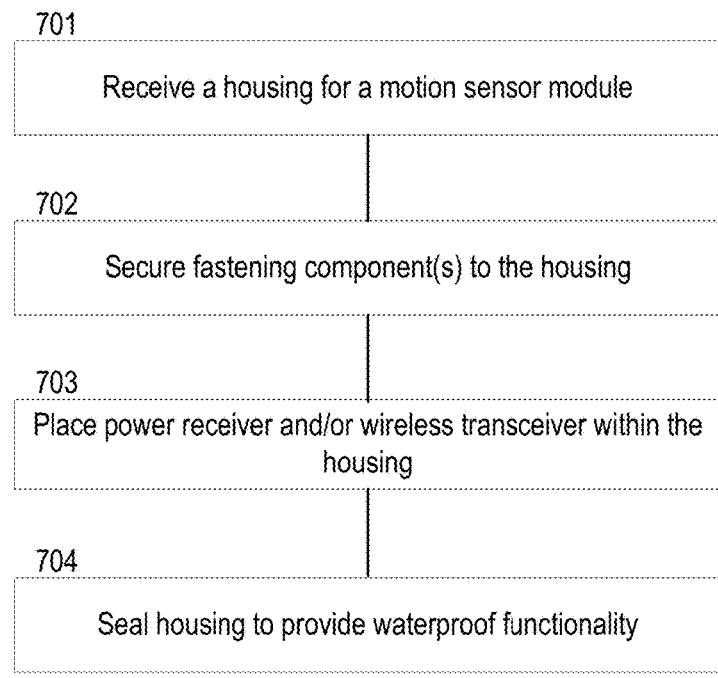
FIG. 7 depicts a process for manufacturing a motion sensor module that can be affixed to a wireless accessory bus of an electronic device.

FIG. 7 depicts a process 700 for manufacturing a motion sensor module that can be affixed to a wireless accessory bus of an electronic device. A housing is initially received (e.g., by a manufacturer) that is designed to protect various internal components (step 701). The internal components can include IMU(s), processor(s), memory, etc.

One or more fastening components can then be secured to the housing (step 702). For example, one or more magnets may be secured to the inner surface of the housing. The magnet(s) permit the motion sensor module to be securely attached to an electronic device without requiring mechanical connectors. As another example, a mechanical clip may be secured to the outer surface of the housing.

The motion sensor module can be designed such that a power receiver and/or a wireless transceiver can be placed within the housing (step 703). As shown in FIG. 3, the fastening component(s), power receiver, and/or wireless transceiver collectively allow the motion sensor module to readily interface with a wireless accessory bus of an electronic device to which the motion sensor module can be magnetically, electrically, and/or communicatively coupled.

In some embodiments, the housing is sealed to provide waterproof functionality (step 704). For example, the housing may be hermetically sealed using an epoxy resin, rubber seals, etc. Some embodiments of the motion sensor module are rated for depths of greater than 10 feet, 50 feet, 100 feet, etc.

Figure 8:
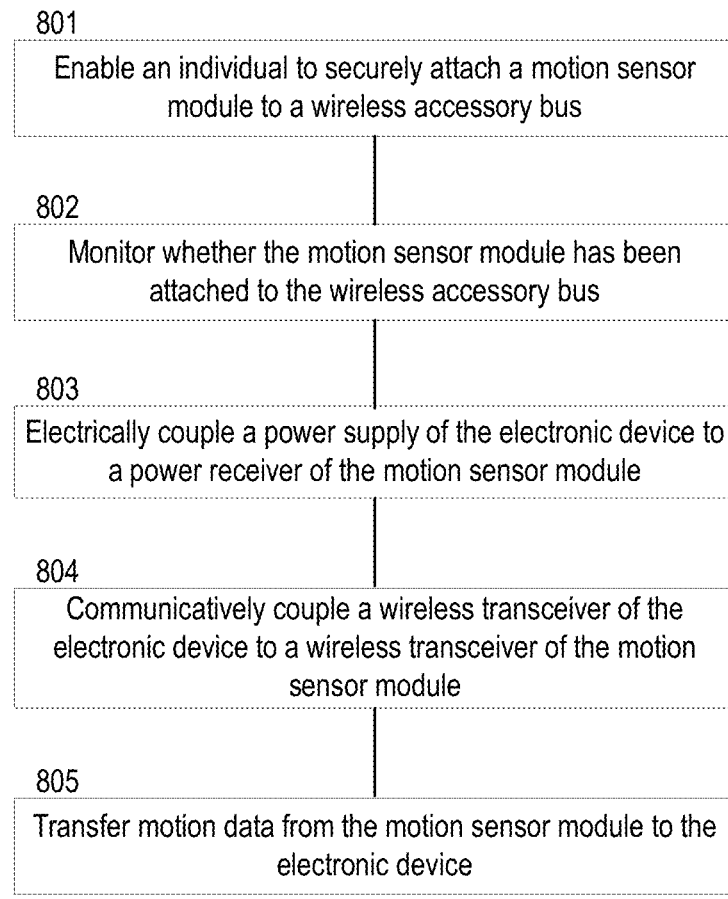
FIG. 8 depicts a process for coupling a motion sensor module to the wireless accessory bus of an electronic device.

FIG. 8 depicts a process 800 for coupling a motion sensor module to the wireless accessory bus of an electronic device. An individual initially acquires a motion sensor module and an electronic device that includes a wireless accessory bus. The electronic device could be, for example, electronic device 200 of FIG. 2 or any other suitable electronic device. The wireless accessory bus enables the individual to securely attach the motion sensor module to the electronic device (step 801).

Typically, the electronic device continually monitors whether the motion sensor module has been attached to the wireless accessory bus (step 802). For example, a processor within the electronic device may be configured to detect when the motion sensor module has been placed on or near the wireless accessory bus. More specifically, a wireless transceiver within the electronic device may be able to detect when another wireless transceiver comes within a certain proximity, thereby indicating the presence of the motion sensor module.

When the motion sensor module is attached to the wireless accessory bus, the electronic device can electrically couple a power supply of the electronic device to a power receiver of the motion sensor module (step 803). For example, the power supply of the electronic device may be coupled to a power transmitter that wirelessly transfers power to the power receiver of the motion sensor module. As another example, an electrical contact of the electronic device may transfer power upon initiating a physical connection with a corresponding electrical contact of the motion sensor module.

The electronic device may also be configured to communicatively couple a wireless transceiver of the electronic device to a wireless transceiver of the motion sensor module (step 804). The wireless transceivers can permit the electronic device and the motion sensor module to communicate with one another without sharing a physical connection. After initiating a communication channel between the electronic device and the motion sensor module, the motion sensor module can transfer motion data to the electronic device (step 805). The motion data may be indicative of movement of the motion sensor module as a whole. For example, the motion data may be generated by one or more IMUs housed within the motion sensor module.

Figure 9:
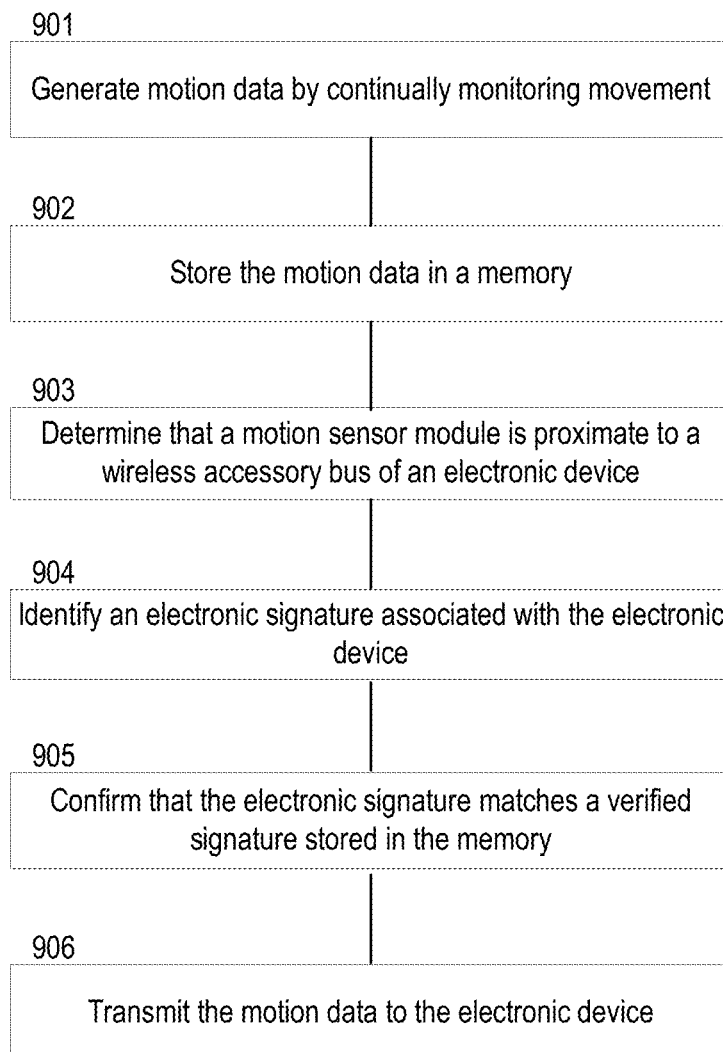
FIG. 9 depicts a process for initiating a transfer of motion data from a motion sensor module to an electronic device.

FIG. 9 depicts a process 900 for initiating a transfer of motion data from a motion sensor module to an electronic device. Initially, the motion sensor module generates motion data by continually monitoring movement (step 901). More specifically, the motion data can be generated by one or more IMUs housed within the motion sensor module.

Motion data generated by the IMU(s) can be stored within a memory (step 902). Generally, the memory resides within the motion sensor module. However, in some embodiments, the memory is accessible to the motion sensor module across a network. The motion sensor module can also periodically or continually determine whether it is positioned in close proximity to a wireless accessory bus of an electronic device (step 903). For example, the motion sensor module may determine whether a wireless transceiver within the motion sensor module is able to detect another wireless transceiver, thereby indicating the presence of the electronic device.

In some embodiments, the motion sensor module identifies an electronic signature associated with the electronic device (step 904). The electronic signature may, for example, be transmitted to the motion sensor module via a communication link established between the wireless transceiver of the motion sensor module and the wireless transceiver of the electronic device. In such embodiments, the motion sensor module can also confirm that the electronic signature matches a verified signature stored in the memory (step 905). Such action ensures that the electronic device has been authorized to receive potentially-sensitive data (e.g., motion data or health data). The motion sensor module can then transmit the motion data to the electronic device (step 906)

Unless contrary to physical possibility, it is envisioned that the steps described above may be performed in various sequences and combinations. For example, a motion sensor module could be configured to periodically or continually transfer data to an electronic device. Other steps may also be included in some embodiments.

Processing System

Figure 10:
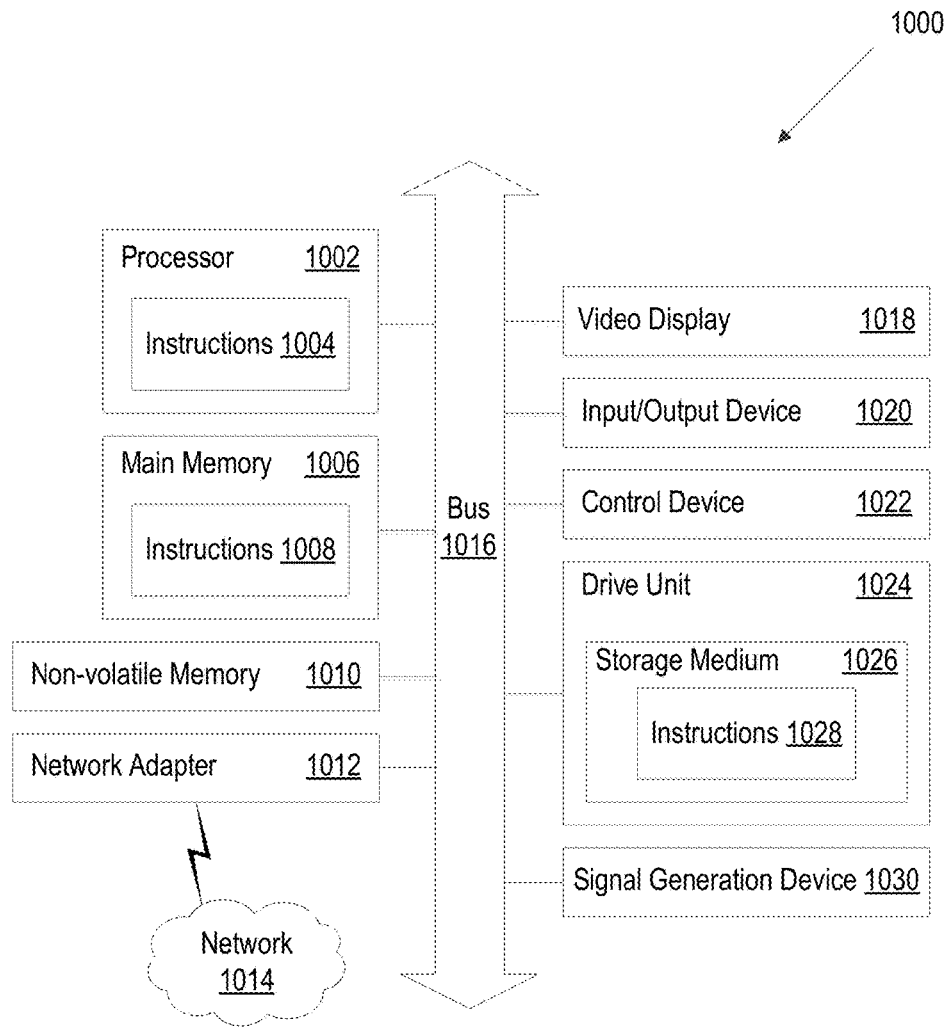
FIG. 10 is a block diagram illustrating an example of a processing system in which at least some operations described herein can be implemented.

FIG. 10 is a block diagram illustrating an example of a processing system 1000 in which at least some operations described herein can be implemented. For example, some components of the processing system 1000 may be hosted on a motion sensor module, while other components of the processing system 1000 may be hosted on an electronic device to which the motion sensor module is communicatively coupled.

The processing system 1000 may include one or more central processing units ("processors") 1002, main memory 1006, non-volatile memory 1010, network adapter 1012 (e.g., network interface), video display 1018, input/output devices 1020, control device 1022 (e.g., keyboard and pointing devices), drive unit 1024 including a storage medium 1026, and signal generation device 1030 that are communicatively connected to a bus 1016. The bus 1016 is illustrated as an abstraction that represents one or more physical buses and/or point-to-point connections that are connected by appropriate bridges, adapters, or controllers. The bus 1016, therefore, can include a system bus, a Peripheral Component Interconnect (PCI) bus or PCI-Express bus, a HyperTransport or industry standard architecture (ISA) bus, a small computer system interface (SCSI) bus, a universal serial bus (USB), IIC (I2C) bus, or an Institute of Electrical and Electronics Engineers (IEEE) standard 1394 bus (also referred to as "Firewire").

The processing system 1000 may share a similar computer processor architecture as that of a desktop computer, tablet computer, personal digital assistant (PDA), mobile phone, game console (e.g., Sony PlayStation® or Microsoft Xbox®), music player (e.g., Apple iPod Touch®), wearable electronic device (e.g., a watch or fitness band), network-connected ("smart") device (e.g., a television or home assistant device), virtual/augmented reality systems (e.g., a head-mounted display such as Oculus Rift® or Microsoft Hololens®), or another electronic device capable of executing a set of instructions (sequential or otherwise) that specify action(s) to be taken by the processing system 1000.

While the main memory 1006, non-volatile memory 1010, and storage medium 1026 (also called a "machine-readable medium") are shown to be a single medium, the term "machine-readable medium" and "storage medium" should be taken to include a single medium or multiple media (e.g., a centralized/distributed database and/or associated caches and servers) that store one or more sets of instructions 1028. The term "machine-readable medium" and "storage medium" shall also be taken to include any medium that is capable of storing, encoding, or carrying a set of instructions for execution by the processing system 1000.

In general, the routines executed to implement the embodiments of the disclosure may be implemented as part of an operating system or a specific application, component, program, object, module, or sequence of instructions (collectively referred to as "computer programs"). The computer programs typically comprise one or more instructions (e.g., instructions 1004, 1008, 1028) set at various times in various memory and storage devices in a computing device. When read and executed by the one or more processors 1002, the instruction(s) cause the processing system 1000 to perform operations to execute elements involving the various aspects of the disclosure.

Moreover, while embodiments have been described in the context of fully functioning computing devices, those skilled in the art will appreciate that the various embodiments are capable of being distributed as a program product in a variety of forms. The disclosure applies regardless of the particular type of machine or computer-readable media used to actually effect the distribution.

Further examples of machine-readable storage media, machine-readable media, or computer-readable media include recordable-type media such as volatile and non-volatile memory devices 1010, floppy and other removable disks, hard disk drives, optical disks (e.g., Compact Disk Read-Only Memory (CD-ROMS), Digital Versatile Disks (DVDs)), and transmission-type media such as digital and analog communication links.

The network adapter 1012 enables the processing system 1000 to mediate data in a network 1014 with an entity that is external to the processing system 1000 through any communication protocol supported by the processing system 1000 and the external entity. The network adapter 1012 can include one or more of a network adaptor card, a wireless network interface card, a router, an access point, a wireless router, a switch, a multilayer switch, a protocol converter, a gateway, a bridge, bridge router, a hub, a digital media receiver, and/or a repeater.

The network adapter 1012 may include a firewall that governs and/or manages permission to access/proxy data in a computer network, and tracks varying levels of trust between different machines and/or applications. The firewall can be any number of modules having any combination of hardware and/or software components able to enforce a predetermined set of access rights between a particular set of machines and applications, machines and machines, and/or applications and applications (e.g., to regulate the flow of traffic and resource sharing between these entities). The firewall may additionally manage and/or have access to an access control list that details permissions including the access and operation rights of an object by an individual, a machine, and/or an application, and the circumstances under which the permission rights stand.

The techniques introduced here can be implemented by programmable circuitry (e.g., one or more microprocessors), software and/or firmware, special-purpose hardwired (i.e., non-programmable) circuitry, or a combination of such forms. Special-purpose circuitry can be in the form of one or more application-specific integrated circuits (ASICs), programmable logic devices (PLDs), field-programmable gate arrays (FPGAs), etc.

Remarks

The foregoing description of various embodiments of the claimed subject matter has been provided for the purposes of illustration and description. It is not intended to be exhaustive or to limit the claimed subject matter to the precise forms disclosed. Many modifications and variations will be apparent to one skilled in the art. Embodiments were chosen and described in order to best describe the principles of the invention and its practical applications, thereby enabling those skilled in the relevant art to understand the claimed subject matter, the various embodiments, and the various modifications that are suited to the particular uses contemplated.

Although the Detailed Description describes certain embodiments and the best mode contemplated, the technology can be practiced in many ways no matter how detailed the Detailed Description appears. Embodiments may vary considerably in their implementation details, while still being encompassed by the specification. Particular terminology used when describing certain features or aspects of various embodiments should not be taken to imply that the terminology is being redefined herein to be restricted to any specific characteristics, features, or aspects of the technology with which that terminology is associated. In general, the terms used in the following embodiments should not be construed to limit the technology to the specific embodiments disclosed in the specification, unless those terms are explicitly defined herein. Accordingly, the actual scope of the technology encompasses not only the disclosed embodiments, but also all equivalent ways of practicing or implementing the embodiments.

The language used in the specification has been principally selected for readability and instructional purposes. It may not have been selected to delineate or circumscribe the subject matter. It is therefore intended that the scope of the technology be limited not by this Detailed Description, but rather by any claims that issue on an application based hereon. Accordingly, the disclosure of various embodiments is intended to be illustrative, but not limiting, of the scope of the technology as set forth in the following claims.

The invention claimed is:

1. A motion sensor module for an electronic device, the motion sensor module comprising:
   a housing;
   an electrical contact configured to receive power from the electronic device upon maintaining a physical connection with a corresponding electrical contact of the electronic device;
   an inertial measurement unit configured to generate motion data indicative of motion of the motion sensor module,
       wherein the inertial measurement unit has a sample rate of at least 100 kilohertz (kHz);
   a memory configured to store the motion data generated by the inertial measurement unit; and
   a wireless transmitter configured to automatically transfer the motion data to the electronic device without requiring user input when the housing is positioned proximate to an accessory bus of the electronic device.

2. The motion sensor module of claim 1, wherein the inertial measurement unit includes an accelerometer, a gyroscope, a magnetometer, or any combination thereof.

3. The motion sensor module of claim 1, further comprising:
   a magnet for maintaining the motion sensor module in a predetermined orientation relative to the wireless accessory bus of the electronic device.

4. The motion sensor module of claim 1, wherein the housing is comprised of a ferromagnetic material that enables the motion sensor module to be maintained in a predetermined orientation relative to a magnet disposed within the electronic device.

5. The motion sensor module of claim 1, further comprising:
   a receiver configured to wirelessly receive information from the electronic device when the housing is positioned proximate to the accessory bus of the electronic device.

6. The motion sensor module of claim 1, further comprising:
   a rechargeable battery configured to output power to the inertial measurement unit; and
   a power gauge configured to determine a present state of charge of the rechargeable battery.

7. The motion sensor module of claim 6, wherein the electrical contact is further configured to route power received from the electronic device to the rechargeable battery.

8. A motion sensor module comprising:
   a housing;
   a magnet, affixed to an inner surface of the housing, configured to maintain the motion sensor module in a predetermined orientation relative to an electronic device when the housing is positioned proximate to the electronic device;
   an inertial measurement unit configured to generate motion data indicative of motion of the motion sensor module,
       wherein the inertial measurement unit has a sample rate of at least 100 kilohertz (kHz); and
   a wireless transceiver configured to automatically communicate with an electronic device via a bi-directional communication channel when the housing is positioned proximate to an accessory bus of the electronic device.

9. The motion sensor module of claim 8, wherein the housing is hermetically sealed to provide waterproof functionality.

10. The motion sensor module of claim 8, further comprising:

a power receiver configured to receive power that is wirelessly transferred to the motion sensor module by a source external from the motion sensor module; and a rechargeable battery configured to output power to the inertial measurement unit.

11. The motion sensor module of claim 10, wherein the source of power is a power supply of the electronic device.

12. The motion sensor module of claim 8, wherein the bi-directional communication channel is established in accordance with any of a Near Field Communication (NFC) protocol, a Bluetooth protocol, a Wi-Fi protocol, a cellular data communication protocol, and a proprietary point-to-point protocol.

13. The motion sensor module of claim 8, wherein the wireless transceiver has a transfer speed of at least 1 gigabit per second (Gbps).

14. The motion sensor module of claim 8, further comprising:

a clock module configured to generate time stamps that accompany the motion data.

15. A computer-implemented method comprising:

generating, by a motion sensor module, motion data by continually monitoring movement of an inertial measurement unit;

storing, by the motion sensor module, the motion data in a memory;

receiving, by the motion sensor module, power from an electronic device at an electrical contact accessible through a housing;

determining, by the motion sensor module, that the motion sensor module is positioned proximate to an accessory bus of the electronic device by detecting that the electrical contact has initiated a physical connection with a corresponding electrical contact of the electronic device; and automatically transmitting, by the motion sensor module, the motion data to the electronic device via a bi-directional communication channel having a transfer speed of at least 1 gigabit per second (Gbps).

16. The computer-implemented method of claim 15, wherein the memory is accessible to the motion sensor module across a network.

17. A computer-implemented method comprising:

generating, by a motion sensor module, motion data by continually monitoring movement of an inertial measurement unit;

storing, by the motion sensor module, the motion data in a memory;

determining, by the motion sensor module, that the motion sensor module is positioned proximate to an accessory bus of an electronic device by identifying an electronic signature associated with the electronic device, and confirming that the electronic signature matches a verified signature stored in the memory; and automatically transmitting, by the motion sensor module, the motion data to the electronic device via a bi-directional communication channel having a transfer speed of at least 1 gigabit per second (Gbps).

* * * * *